United States Patent [19]

Kirkman et al.

[11] Patent Number: 5,461,228
[45] Date of Patent: Oct. 24, 1995

[54] OPTICAL INSPECTION OF CONTAINER DIMENSIONAL PARAMETERS USING A TELECENTRIC LENS

[75] Inventors: James A. Kirkman, Oregon; James A. Ringlien, Maumee, both of Ohio

[73] Assignee: Owens-Brockway Glass Container Inc., Toledo, Ohio

[21] Appl. No.: 224,359

[22] Filed: Apr. 7, 1994

[51] Int. Cl.⁶ .......................... G01N 21/00; G01N 21/90
[52] U.S. Cl. ...................................... 250/223 B; 356/240
[58] Field of Search ........................ 250/223 B, 223 R; 356/240, 428; 209/524, 526; 359/663

[56] References Cited

U.S. PATENT DOCUMENTS

| | | |
|---|---|---|
| 3,313,409 | 4/1967 | Johnson . |
| 4,083,637 | 4/1978 | Ellinger et al. ........................ 356/240 |
| 4,256,957 | 3/1981 | Ford et al. . |
| 4,376,951 | 3/1983 | Miyazawa . |
| 4,386,828 | 6/1983 | Hirose . |
| 4,435,641 | 3/1984 | Hajime . |
| 4,492,476 | 1/1985 | Miyazawa . |
| 4,526,443 | 7/1985 | Hirose . |
| 4,580,045 | 4/1986 | Kulig ................................ 250/223 B |
| 4,682,220 | 7/1987 | Beurskens . |
| 4,762,544 | 8/1988 | Davey . |
| 4,792,695 | 12/1988 | Blandford . |
| 4,850,045 | 7/1989 | Funke . |
| 4,906,098 | 3/1990 | Thomas et al. . |
| 4,958,223 | 9/1990 | Juvinall . |
| 4,959,537 | 9/1990 | Kimoto et al. ..................... 250/223 B |
| 5,008,743 | 4/1991 | Katzir et al. . |

*Primary Examiner*—Edward P. Westin
*Assistant Examiner*—Que T. Le

[57] ABSTRACT

Apparatus for inspecting the inside diameter of a container mouth that includes a light source for directing light energy into the container, and a light sensor disposed with respect to the source and the container to receive light energy transmitted out of the container through the mouth. A telecentric lens directs onto the light sensor light energy transmitted through the container mouth substantially axially of the container mouth. The light energy is focused through an iris onto a matrix array sensor, which develops a two-dimensional image of the container mouth. The matrix array sensor is coupled to image processing electronics for determining or calculating a circle of greatest diameter that will fit within the two-dimensional image of the container mouth, and treating such circle as indicative of the effective diameter of the container mouth.

14 Claims, 1 Drawing Sheet

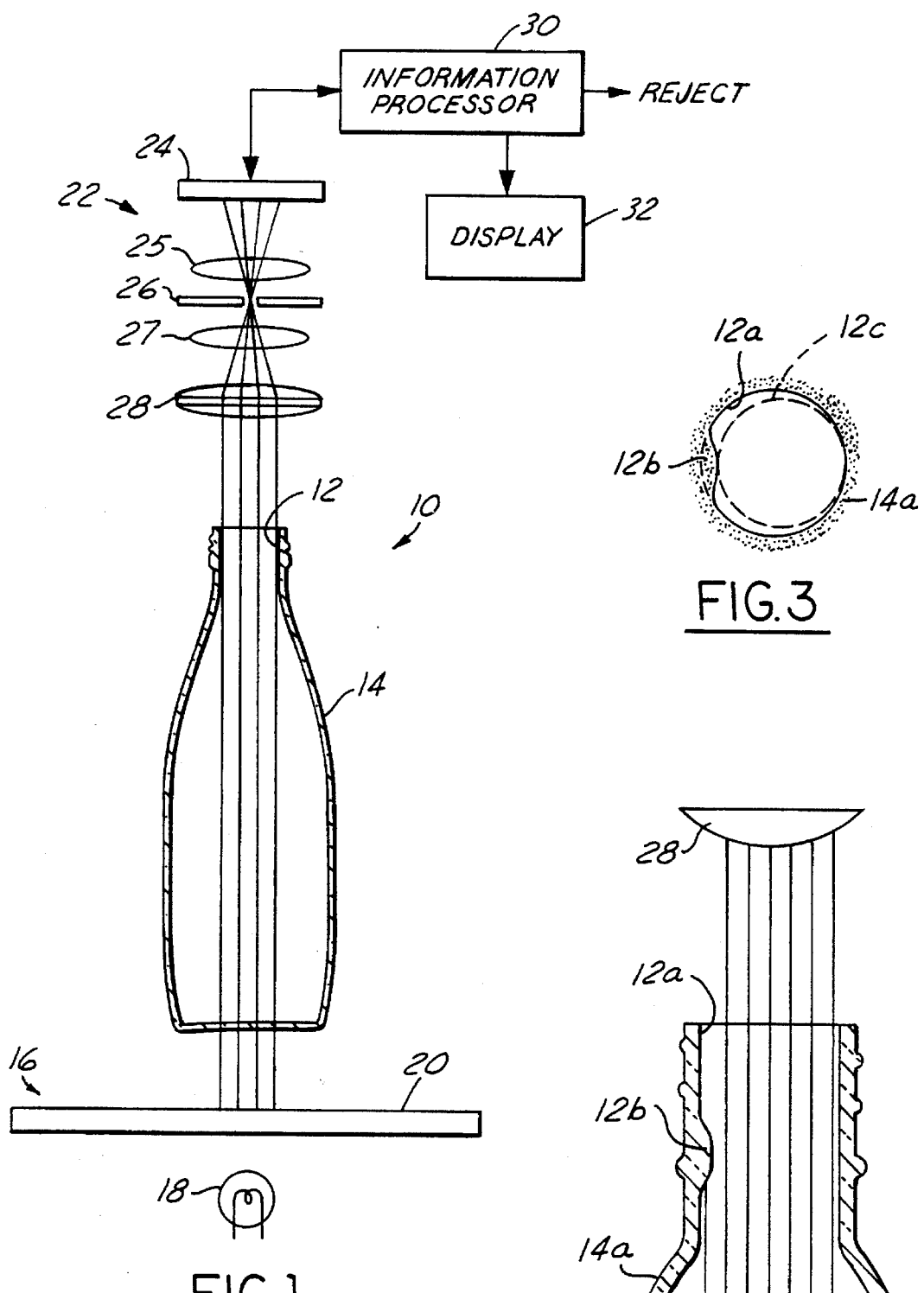
FIG.1
FIG.3
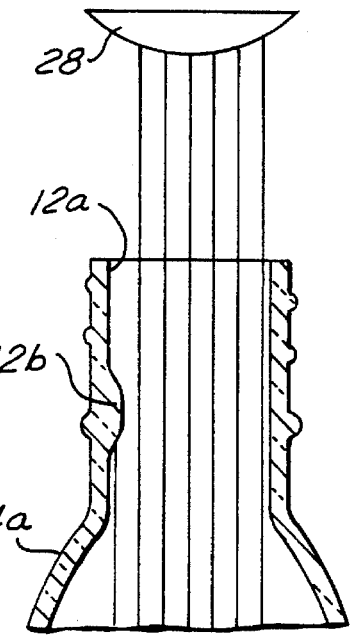
FIG.2

OPTICAL INSPECTION OF CONTAINER DIMENSIONAL PARAMETERS USING A TELECENTRIC LENS

The present invention is directed to non-contact measurement of container dimensional parameters, and more particularly to an apparatus and method for optical measurement of the inside diameter of a container mouth.

BACKGROUND AND OBJECTS OF THE INVENTION

In the manufacture of translucent containers such as clear or colored glass bottles, it is important to maintain dimensional parameters of each container within design specifications for both functional and aesthetic reasons. For example, it is important that the finish of the container, including particularly the container mouth, possess desired geometric characteristics so that the container can be accepted by automatic filling and capping equipment without damage to the equipment, fracture of the container or jamming of the process line.

U.S. Pat. No. 3,313,409, assigned to the assignee hereof, discloses a container inspection system in which containers are routed in sequence through a plurality of inspection stations at which various geometric and other properties are measured. At one such station, an attempt is made to insert a plug of predetermined size into the mouth of the container. The diameter of the plug is coordinated with minimum container mouth diameter for mating with container filling equipment, for example. If the plug cannot be so inserted into the container mouth, the container is rejected. At other stations of the inspection system, container dimensional parameters are measured by monitoring the position of rollers in contact with the container as the container is rotated.

Although the system disclosed in the noted patent has enjoyed substantial commercial acceptance and success, improvements remain desirable. The inspection techniques that require physical contact with the container are slow, and are subject to mechanical wear of the rollers and plugs, for example. The reciprocating motions needed to bring the plugs and rollers into and out of contact with the container draw substantial amounts of electrical power. It is a general object of the present invention to provide an apparatus and method for inspection of container parameters, including particularly inside diameter of the container mouth, that have no moving parts (other than the container itself) or parts in contact with the container, that are more economical and efficient than inspection techniques heretofore proposed, and afford reliable service over an extended operating lifetime.

SUMMARY OF THE INVENTION

Apparatus for inspecting a dimensional parameter of a container includes a light source for directing light energy onto the container and a light sensor disposed to receive an image of at least that portion of the container illuminated by the light source. A telecentric lens directs onto the light sensor energy traveling in a direction parallel to the axis of the telecentric lens, so that the illuminated portion of the container appears as a dark image against a light background. The telecentric lens arrangement in the preferred embodiment of the invention includes an iris, and a lens having one focus at infinity adjacent to the container and a second focus at the iris.

Apparatus for inspecting the inside diameter of a container mouth in accordance with the preferred embodiment of the invention comprises a light source for directing light energy into the container, and a light sensor disposed with respect to the source and the container to receive light energy transmitted out of the container through the mouth, in effect rejecting light rays that are not parallel to the container axis. A telecentric lens directs onto the light sensor light energy transmitted through the container mouth substantially axially of the container mouth. The light energy is focused through an iris onto a matrix array sensor, which develops a two-dimensional image of the container mouth. The matrix array sensor is coupled to image processing electronics for determining or calculating a circle of greatest diameter that will fit within the two-dimensional image of the container mouth, and treating such circle as indicative of the effective diameter of the container mouth.

A method of inspecting the inside diameter of a container mouth in accordance with the present invention thus includes the steps of directing light energy through the container and out of the container mouth, directing onto a light sensor substantially only light energy emerging from the container mouth in a direction axially of the mouth, and determining inside diameter of the container mouth as a function of such light energy directed onto the sensor. Mouth inside diameter is determined by developing a two-dimensional image of the container mouth as a function of the light energy directed on the sensor, and determining or calculating a circle of greatest diameter that will fit within the image of the container mouth. This circle is then treated as defining the effective inside diameter of the container mouth. In the event that the mouth inside diameter so determined is less than the desired minimum diameter, the container is rejected.

BRIEF DESCRIPTION OF THE DRAWING

The invention, together with additional objects, features and advantages thereof, will be best understood from the following description, the appended claims and the accompanying drawing in which:

FIG. 1 is a schematic diagram of an electro-optical non-contact system for measuring inside diameter of a container mouth in accordance with a presently preferred implementation of the invention;

FIG. 2 is a fragmentary schematic diagram of a portion of FIG. 1 on an enlarged scale; and FIG. 3 is a schematic diagram that illustrates calculation of effective inside diameter from a two-dimensional image of the container mouth.

DETAILED DESCRIPTION OF PREFERRED EMBODIMENT

FIG. 1 illustrates apparatus 10 for inspecting or measuring the inside diameter of the mouth 12 of a container 14 in accordance with a presently preferred implementation of the invention. A light source 16 includes a lamp 18 and a diffuser 20 for directing diffused light energy into the container from beneath the container in a direction generally parallel to the axis of the container and the container mouth. A camera 22 is positioned above container 14 in axial alignment with container mouth 12. Camera 22 includes a matrix array CCD sensor 24, an entrance pupil 26 and lenses 25,27 associated with the entrance pupil. A telecentric lens 28 is positioned between camera 22 and mouth 12 of container 14. Telecentric lens 28 has a first focus in the direction of container 14 at infinity, and a second focus at entrance pupil 26. That is, camera 22 is positioned with respect to lens 28 so that entrance pupil 26 is spaced from lens 28 by the focal distance of the lens. Thus, pupil 26 with lenses 25,27 functions as an iris in combination with lens 28 for focusing onto sensor 24 essentially only light rays that emerge from container mouth 12 essentially parallel to the axis of the container, lens and camera. That is, light rays that emerge from the container mouth in a direction not parallel to the container and optical axis will be directed by lens 28 other than through pupil 26, and thus effectively blocked from impingement on sensor 24. In this way, a clear image of the container mouth is focused onto matrix array sensor 24.

Sensor 24 is connected to information processing electronics 30 for scanning the sensor and developing a two-dimensional image of the container mouth. The glass that defines the container mouth will appear as a dark image against a bright background formed by the light energy transmitted through the container mouth. This is because the glass of the container refracts light transmitted into the body of the container, and this refracted light will not be parallel to the optical axis and thus not be directed onto sensor 24. Exemplary techniques for scanning a matrix array sensor and developing a two-dimensional image of a container mouth are disclosed in U.S. Pat. No. 4,958,223.

FIGS. 2–3 illustrate operation of the invention in connection with a container 14a having a mouth 12a with a choked region 12b. As illustrated in FIG. 2, choked region 12b blocks a portion of the light rays emerging from the container mouth parallel to the container/optical axis, thereby creating at sensor 24 and image information processor 30 a two-dimensional image as illustrated in FIG. 3. Information processor 30 analyzes the image of FIG. 3 by calculating a circle 12c of greatest diameter that will fit within the image of mouth 12a, including the choked region 12b. The calculated circle 12c is then treated as the effective inside diameter of the container mouth. In the event that such effective diameter is less than minimum desired diameter, information processor 30 supplies an appropriate signal to a reject mechanism for removing container 14 from the inspection conveyor line. Information processor 30 is also coupled to a display 32 for displaying the two-dimensional image of the container under inspection, or other appropriate inspection information.

In addition to provide an essentially go/no-go indication of an acceptable container mouth inside diameter as described above, the measurement data may be employed for purposes of process analysis, or for controlling the container forming process as disclosed in U.S. Pat. No. 4,762,544. The invention may also be employed for measuring other container parameters and geometric characteristics. For example, a so-called "leaner" container—i.e., a container in which the mouth 12 is cocked with respect to the optical axis of the inspection apparatus—will produce an image of two overlapping circles from opposed edges of the container mouth at the top and bottom of the container neck. If the effective diameter across these overlapping circles is too small, the container would be rejected as having an effective mouth diameter less than the desired minimum. The apparatus of the invention may also be employed to detect and reject a container having a so-called "bird swing" variation if the variation were sufficiently large to be viewed across the mouth of the container.

We claim:

1. Apparatus for inspecting a container having an open mouth, said apparatus comprises:

a light source for directing light energy into the container and light sensing means disposed with respect to said light source and the container to receive light energy transmitted through the container mouth, said light sensing means comprising telecentric lens means for directing to said light sensing means light energy transmitted through the container mouth substantially axially of the container mouth.

2. The apparatus set forth in claim 1 wherein said telecentric lens means comprises a lens having a predetermined focal distance remote from the container, and an iris spaced from said lens by said focal distance.

3. The apparatus set forth in claim 1 wherein said telecentric lens means comprises a lens having a focus at infinity in the direction of the container and a focus remote from the container at a predetermined focal distance, and an iris positioned remotely of the container at said predetermined focal distance from said lens, such that said lens focuses through said iris light energy transmitted through the container mouth substantially axially of the container mouth.

4. The apparatus set forth in claim 3 wherein said light sensing means further comprises a light sensor positioned to receive an image of the container mouth by means of light focused through said iris by said lens.

5. The apparatus set forth in claim 4 wherein said light sensor comprises a matrix array sensor and means coupled to said sensor for developing a two-dimensional image of the container mouth.

6. The apparatus set forth in claim 5 wherein said light sensing means further comprises means for analyzing said image to determine inside diameter of the container mouth.

7. The apparatus set forth in claim 6 wherein said analyzing means comprises means for determining a circle of greatest diameter that will fit within said image.

8. The apparatus set forth in claim 7 further comprising means for indicating acceptability of the container as a function of said circle of greatest diameter.

9. A method of inspecting a container having an open mouth, comprising the steps of:

(a) directing light energy through the container and out of the container mouth, (b) directing onto a light sensor substantially only light energy emerging from the container mouth in a direction axially of the mouth, and (c) determining at least one geometric property of the container mouth as a function of light energy directed on said sensor.

10. The method set forth in claim 9 wherein said step (c) comprises the steps of:

(c1) developing a two-dimensional image of the container mouth as a function of light energy directed onto said sensor in said step (b), and (c2) determining said geometric property as a function of said two-dimensional image.

11. The method set forth in claim 10 wherein said step (c2) comprises the step of analyzing said two-dimensional image to determine inside diameter of the container mouth.

12. The method set froth in claim 11 wherein said step (c2) is carried out by determining a circle of greatest diameter that will fit within said image and treating said circle as defining the effective diameter of the container mouth.

13. Apparatus for inspecting a dimensional parameter of a container comprising:

a light source for directing light energy onto the container and light sensing means disposed to receive an image of at least that portion of the container illuminated by the light source, said light sensing means comprising telecentric lens means for directing to said light sensing means substantially only light energy parallel to said telecentric lens means such that the illuminated portion of the container appears as a dark image against a light background at said light sensing means.

14. The apparatus set forth in claim 13 wherein said light sensing means comprises a camera having an entrance pupil, and wherein said telecentric lens means has one focus at infinity and a second focus at said pupil.

* * * * *